United States Patent
Peichel et al.

(10) Patent No.: US 6,721,592 B2
(45) Date of Patent: Apr. 13, 2004

(54) AUTOMATIC ELECTROGRAM MEASUREMENT

(75) Inventors: David Peichel, Minneapolis, MN (US); Tho Huynh, Mesa, AZ (US); Forrest C. M. Pape, New Brighton, MN (US); Robert A. Neumann, Blaine, MN (US); John C. Stroebel, Blaine, MN (US); Robert A. Gabler, New Brighton, MN (US); James E. Willenbring, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 200 days.

(21) Appl. No.: 09/952,717

(22) Filed: Sep. 12, 2001

(65) Prior Publication Data

US 2003/0050564 A1 Mar. 13, 2003

(51) Int. Cl.7 .................. A61B 5/0452; A61B 5/0456
(52) U.S. Cl. ................ 600/509; 600/517; 600/521
(58) Field of Search .................. 600/509, 517, 600/521; 607/9

(56) References Cited

U.S. PATENT DOCUMENTS

| | | | |
|---|---|---|---|
| 4,513,743 A | 4/1985 | Van Arragon et al. | 607/27 |
| 5,042,499 A * | 8/1991 | Frank et al. | 600/509 |
| 5,330,513 A | 7/1994 | Nichols et al. | 607/32 |
| 5,350,411 A | 9/1994 | Ryan et al. | 607/32 |
| 5,513,644 A | 5/1996 | McClure et al. | 600/521 |
| 5,562,711 A | 10/1996 | Yerich et al. | 607/17 |
| 5,722,999 A | 3/1998 | Snell | 607/32 |
| 5,957,857 A | 9/1999 | Hartley | 600/521 |
| 6,115,630 A * | 9/2000 | Stadler et al. | 600/521 |
| 6,192,275 B1 | 2/2001 | Zhu et al. | 607/28 |
| 6,263,246 B1 | 7/2001 | Goedeke et al. | 607/60 |
| 6,377,844 B1 * | 4/2002 | Graen | 600/521 |
| 2002/0115938 A1 * | 8/2002 | Hannula | 600/509 |

* cited by examiner

Primary Examiner—Carl Layno
(74) Attorney, Agent, or Firm—Girma Wolde-Michael; Michael C. Soldner (57) ABSTRACT

Techniques for monitoring the magnitudes of representative filtered EGM signals over time. In a typical implementation, a group of digital peak values is generated in a time period and a representative digital peak value is selected for the time period. By comparing representative peak values for several time periods, changes in signal efficacy can be identified.

34 Claims, 8 Drawing Sheets

AUTOMATIC ELECTROGRAM MEASUREMENT

FIELD

The invention relates to implanted medical devices, and in particular, implanted medical devices that monitor cardiac signals.

BACKGROUND

In the medical fields of cardiology and electrophysiology, many tools are used to assess the condition and function of a patient's heart from observed frequency, polarity and amplitudes of the PQRST complex associated with a heart cycle. One such tool is the electrogram (EGM), which is an electrical signal from a region of the heart. An electrogram may be used by many implantable devices that monitor cardiac signals, such as a cardiac pacemaker or an implantable cardioverter/defibrillator (ICD).

An EGM that records the activity of an atrium of the heart is called an atrial EGM, or A-EGM. An A-EGM signal usually includes one prominent peak magnitude corresponding to atrial depolarization, also known as the P-wave. An EGM that records the activity of a ventricle of the heart is called a ventricular EGM, or V-EGM. A V-EGM usually includes one prominent peak magnitude as well, but the peak of the V-EGM corresponds to ventricular depolarization, also known as the R-wave.

Detection of P-waves and R-waves is important in sensing cardiac rates and rhythms. Bradycardia, tachyarrhythmia, premature atrial contraction, premature ventricular contraction, heart block and fibrillation are some of the conditions that may be monitored through sensing P-waves, R-waves, or both.

In a typical cardiac monitor, A-EGM signals and V-EGM signals are filtered and amplified, and are then compared to a sense threshold. When the filtered A-EGM signal exceeds the atrial sense threshold, the implanted device generates a signal indicating that a P-wave has been detected. Similarly, when the filtered V-EGM signal exceeds the ventricular sense threshold, the implanted device generates a signal indicating that an R-wave has been detected.

In some patients, the magnitudes of the cardiac signals change over the long term. The peaks of a V-EGM signal in a patient, for example, may decrease over a period of months. The downward change of signal magnitudes may have many causes.

The prior art includes many techniques for monitoring cardiac signals. For example, U.S. Pat. No. 4,513,743 to van Arragon et al. describes storing and presenting data such as peak QRS amplitudes and peak P amplitudes, and arranging the data for presentation in a histogram. Similarly, U.S. Pat. No. 5,722,999 to Snell describes a system for acquiring and displaying medical data, such as graphing R-wave amplitudes over several months.

Monitoring signal magnitudes relative to sense thresholds has also been described in various contexts. U.S. Pat. No. 4,708,144 to Hamilton, et al., for example, discloses adjusting pacemaker sensitivity in response to peak R-wave values. U.S. Pat. No. 5,330,513 to Nichols et al. describes a sensing threshold analysis that involves monitoring average peak values over a programmed time interval.

U.S. Pat. No. 5,513,644 to McClure et al. describes short-term monitoring of peak values of electrogram signals, and automatically adjusting system sensitivity in response to the signals. U.S. Pat. No. 5,957,857 to Hartley discloses adjustment of amplifier gain in response to peak values of P-waves or R-waves. U.S. Pat. No. 6,192,275 to Zhu et al. describes adjusting the sensitivity of an evoked response threshold, in response to fluctuations in R-wave amplitudes due to factors such as respiration and activity level.

Signal processing techniques related to processing EGM signals are well known. In addition to the patents described above, U.S. Pat. No. 5,350,411 to Ryan et al. illustrates how an A-EGM signal may undergo different processing operations in parallel. V-EGM signals likewise may be processed along different paths simultaneously.

SUMMARY

The invention is directed to techniques for tracking the magnitudes of representative filtered EGM signals so that the magnitudes can be monitored over time. Usually the monitoring is over several days at least. The signal that is monitored is not a raw EGM signal, but rather a filtered EGM signal having the same frequency components as the EGM signal supplied to the sense amplifier.

The invention provides techniques for generating digital peak values. From a group of digital peak values generated in a time period, such as one day, a representative digital peak value is selected.

Peak values can be captured by signal processing circuitry that includes filters, a peak detector, a sample-and-hold circuit that captures the magnitude of the peak, and an analog-to-digital converter that generates a digital peak value as a function of the magnitude of the peak. A processor may validate the peak values and select a peak value as representative of the plurality of peak values. The representative peak value may be selected from the plurality of peak values, for example, or may be selected by mathematical techniques.

In an exemplary implementation, five digital peak values are generated each day. Each digital peak value comes from a single cardiac signal and represents a true intrinsic sensed event. From this collection of five digital peak values, one is selected as the representative peak value of the day. For example, the median value among the five digital peak values may be selected as the representative peak value of the day.

By comparing representative peak values for several time periods, changes in signal strength and efficacy can be identified. Of particular concern is signal attenuation, i.e., a downward change of signal magnitudes. Substantial attenuation of peak values may lead to undersensing of valid P-waves or R-waves, and cause detection failure. In many cases, attenuation may be indicative of changing conditions such as a change in the position of the sensing electrode, a failure of the electrode or a change in the cardiac tissue.

The representative peak values over time may be monitored. If a representative peak value falls below an alert threshold, an alert may be generated notifying the patient and/or the patient's physician of a potential decline in signal efficacy. In addition, several peak values may be presented in a format that allows the values to be compared to each other over time. The physician may use this data to diagnose the condition of the patient, conduct additional diagnostic tests, adjust the therapy for the patient or perform some other appropriate action. In addition, the implanted device may adjust sensitivity to EGM signals by adjusting sense thresholds. An advantage of the invention, therefore, is that it automatically collects data that assists the patient and the physician in diagnosing physiologic conditions, establishing therapy, and troubleshooting the implanted device.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

The invention presents techniques that monitor the efficacy of cardiac signals sensed by an implanted medical device. In particular, the invention presents techniques for sensing changes in signal amplitude, such as signal attenuation. Signal attenuation may cause difficulties for implanted medical devices that include electrodes that sense cardiac electrical activity and sense amplifiers that filter and amplify the signals and compare the signals to sense thresholds.

Such devices include an ICD, which senses cardiac signals and may apply pacing, cardioversion and/or defibrillation therapies in response to the signals. Other devices that provide therapy in response to cardiac signals include a pacemaker implanted pulse generator (IPG) and an implanted pump that administers medication in response to detected arrhythmias. A further device that receives cardiac signals is an implantable monitor, which may monitor the signals but may not be equipped to provide therapy. The invention may be practiced in these and other implementations.

In medical devices that sense cardiac electrical activity, the magnitudes of typical cardiac signals may be monitored over a short term, e.g., from beat to beat. A change in the magnitude of a cardiac signal in the short term may indicate a condition such as fibrillation or tachycardia. A change in the rate or rhythm of the signals in the short term may indicate conditions such as tachycardia or arrhythmia.

Over a longer term, the magnitudes of typical signals may change. Typical signal magnitudes may be fairly constant from day to day, but the magnitudes may change from week to week or from month to month. Of particular concern is signal attenuation, i.e., a tendency of signal magnitudes to become smaller over time. As signal magnitudes decline, there is an increased risk that the medical device will be unable to sense a valid cardiac signal, due to the failure of the signal to exceed the sense threshold.

The downward tendency of typical signal magnitudes may be caused by one or more factors. A change in electrode placement or electrode failure may cause typical signal magnitudes to decline over time. Signal attenuation may also be caused by a slowly occurring change in the quality of the cardiac tissue.

The present invention presents techniques for identifying changes in the magnitudes of typical signals over the long term. When signal attenuation is identified, the patient and the patient's physician may perform additional tests to determine the cause of the attenuation, and may take corrective action.

Figure 1:
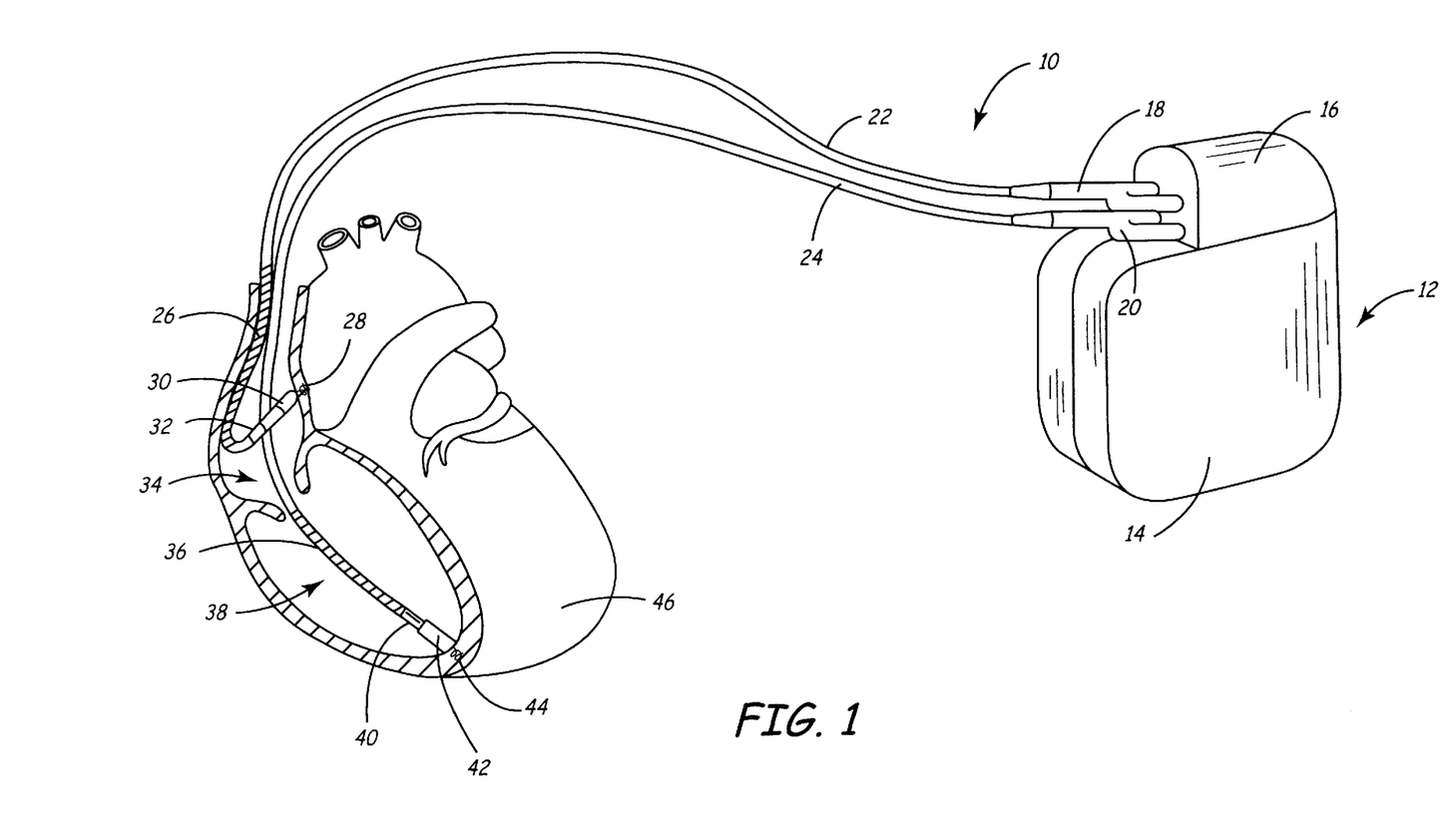
FIG. 1 is a diagram illustrating an implantable defibrillator and lead system.

FIG. 1 illustrates an example implanted defibrillator and lead system 10 in which the present invention may be practiced. System 10 is shown in association with human heart 46. As noted above, the invention is not limited to the exemplary device or system shown in FIG. 1, but may be practiced in a wide variety of implementations.

System 10 comprises a ventricular lead, which includes elongated insulative lead body 24, carrying three concentric coiled conductors separated from one another by tubular insulative sheaths. The distal end of the ventricular lead is deployed in right ventricle 38. Located adjacent the distal end of the ventricular lead are ring electrode 40, extendable helix electrode 44, mounted retractably within insulative electrode head 42, and elongated (approximately 5 cm) defibrillation coil electrode 36. Defibrillation electrode 36 may be fabricated from many materials, such as platinum or platinum alloy. Each of the electrodes is coupled to one of the coiled conductors within lead body 24.

Electrodes 40 and 44 are employed for cardiac pacing and for sensing ventricular depolarizations. Accordingly, electrodes 40 and 44 serve as sensors for a V-EGM. At the proximal end of the ventricular lead is bifurcated connector 20 that carries three electrical connectors, each coupled to one of the coiled conductors.

The atrial/superior vena cava (SVC) lead includes elongated insulative lead body 22, carrying three concentric coiled conductors, separated from one another by tubular insulative sheaths, corresponding to the structure of the ventricular lead. The distal end of the atrial/SVC lead is deployed in right atrium 34. Located adjacent the distal end of the atrial/SVC lead are ring electrode 32 and extendable helix electrode 28, mounted retractably within insulative electrode head 30. Each of the electrodes is coupled to one of the coiled conductors within lead body 22. Electrodes 28 and 32 are employed for atrial pacing and for sensing atrial depolarizations. Accordingly, electrodes 28 and 32 serve as sensors for an A-EGM.

The strength of EGM signals sensed by electrodes 28, 32, 40 and 44 is a function of several factors. One factor affecting the signals is electrode placement. Electrodes 40 and 44, for example, have been placed proximal to apex 45 of heart 46, and may satisfactorily sense ventricular activity in this placement. If electrodes 40 and 44 should shift position, however, signal strength may decline, and sensation of ventricular activity may not be as robust. Electrode failure is another factor that may affect signal strength.

A further factor affecting signal strength is the health of patient's heart 46 itself. A change in the cardiac substrate may affect the electrical characteristics of the cardiac tissue, and consequently may cause a decline in signal strength. For example, the cardiac tissue may die due to ischemia or myocardial infarction, and may no longer conduct signals that reflect cardiac activity.

Elongated coil electrode 26 is provided proximal to electrode 32 and coupled to the third conductor within the lead body 22. Electrode 26 preferably is 10 cm in length or greater and is configured to extend from the SVC toward the tricuspid valve. At the proximal end of the lead is a bifurcated connector 18 which carries three electrical connectors, each coupled to one of the coiled conductors.

ICD 12 is shown in combination with the leads, with lead connector assemblies 18 and 20 inserted into connector block 16. Optionally, insulation of the outward facing portion of housing 14 of ICD 12 may be provided using a plastic coating, e.g., parylene or silicone rubber, as is employed in some unipolar cardiac pacemakers. However, the outward facing portion may instead be left uninsulated, or some other division between insulated and uninsulated portions may be employed. The uninsulated portion of the housing 14 optionally serves as a subcutaneous defibrillation electrode, used to defibrillate either the atria or ventricles.

Electrical stimulation may be indicated when the implantable device detects an arrhythmia. It is therefore important to recognize when the patient is experiencing an arrhythmia. When the magnitudes of A-EGM signals and/or V-EGM signals decline over time, undersensing may occur and valid P-waves and/or R-waves may not be detected. One possible consequence of undersensing is that ICD 12 may interpret the undersensing as a normal rhythm, when in fact the patient is experiencing an arrhythmia. As a result, ICD 12 may refrain from applying stimulation to treat the arrhythmia.

Figure 2:
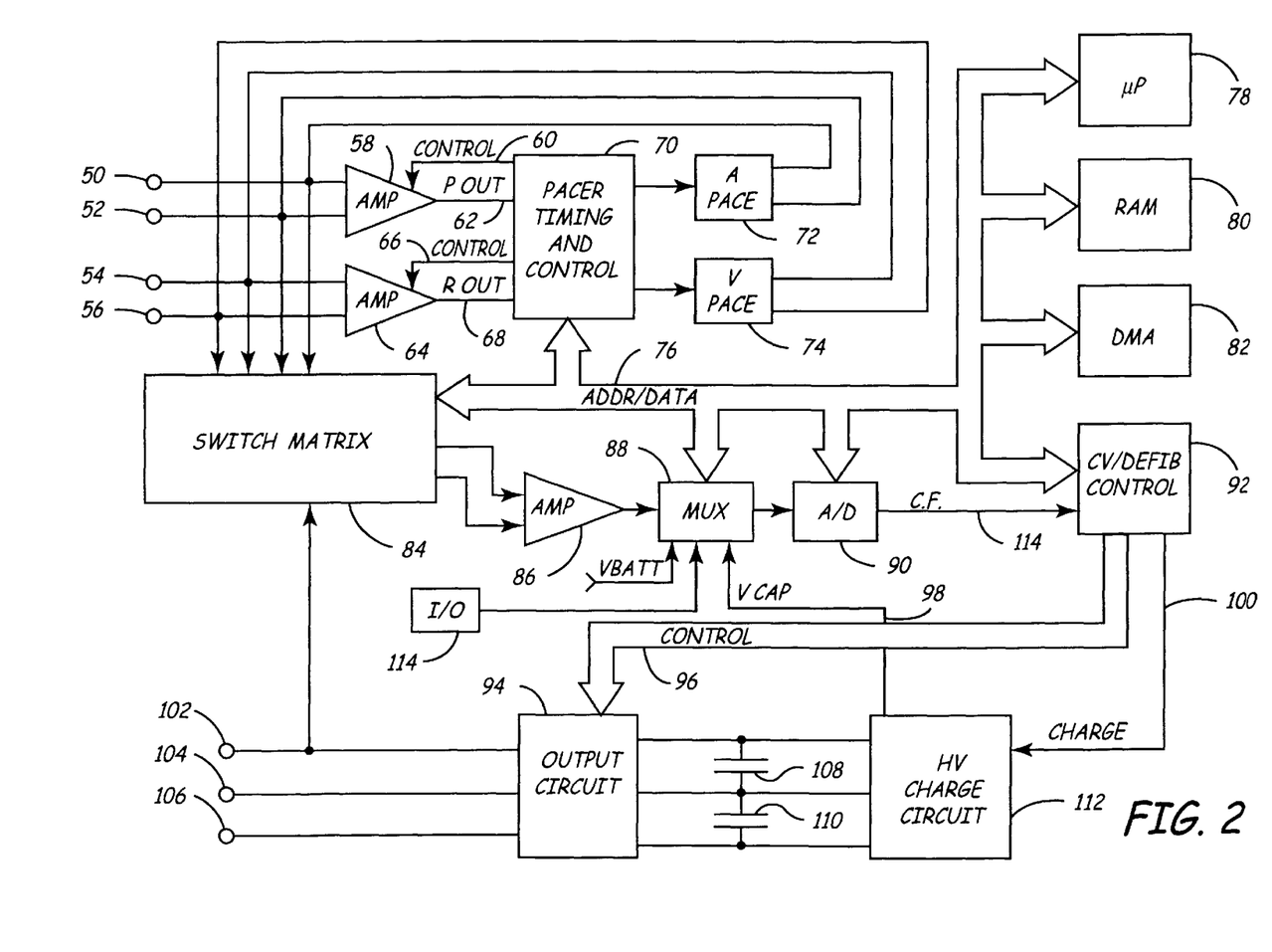
FIG. 2 is a functional schematic diagram of an implantable ICD.

FIG. 2 is a functional schematic diagram of an ICD, in which the present invention may be practiced. FIG. 2 should be taken as exemplary of one type of device in which the invention may be embodied. The invention is not limited to the exemplary device shown in FIG. 2, but may be practiced in a wide variety of device implementations, such as a pacemaker or an implantable monitor.

FIG. 2 is one possible functional representation of system 10 shown in FIG. 1. The representation put forth in FIG. 2 is not limited to system 10 shown in FIG. 1, however, and the invention is not limited to the representation shown in FIG. 2. The invention may be practiced in a system that includes more or fewer features than are depicted in FIG. 2.

The device illustrated in FIG. 2 is provided with an electrode system including electrodes as illustrated in FIG. 1. For clarity of analysis, the pacing/sensing electrodes 50, 52, 54 and 56 are shown as logically separate from pacing/defibrillation electrodes 102, 104 and 106.

Electrodes 102, 104 and 106 correspond to an atrial defibrillation electrode, a ventricular defibrillation electrode and the uninsulated portion of the housing of the ICD. Electrodes 102, 104 and 106 are coupled to high voltage output circuit 94. High voltage output circuit 94 includes high voltage switches controlled by cardioversion/defibrillation (CV/defib) control logic 92 via control bus 96. The switches within output circuit 94 control which electrodes are employed and which are coupled to the positive and negative terminals of the capacitor bank including capacitors 108 and 110 during delivery of the defibrillation pulses.

Electrodes 54 and 56 are located on or in the ventricle and are coupled to R-wave sense amplifier 64. Operation of amplifier 64 is controlled by pacer timing/control circuitry 70 via control lines 66. Amplifier 64 performs functions in addition to amplification, such as filtering the signals sensed by electrodes 54 and 56. Amplifier 64 also includes a comparator that compares the input signal to a pre-selected ventricular sense threshold. A signal is generated on R-out line 68 whenever the signal sensed between electrodes 54 and 56 exceeds the ventricular sense threshold.

Electrodes 50 and 52 are located on or in the atrium and are coupled to P-wave sense amplifier 58. Operation of amplifier 58 is controlled by pacing circuitry 70 via control lines 60. Amplifier 58 performs functions in addition to amplification, such as filtering the signals sensed by electrodes 50 and 52. Amplifier 58 includes a comparator that compares the input signal to a pre-selected atrial sense threshold, which can be different from the ventricular sense threshold. A signal is generated on P-out line 62 whenever the signal sensed between electrodes 50 and 52 exceeds the atrial sense threshold.

In some patients, further pacing and/or sense electrodes may be implanted in addition to electrodes 52, 54, 56 and 58. Additional electrodes allow measurement of sense vectors, i.e., measurement of the magnitude and direction of atrial or ventricular electrical activity between a pair of electrodes. Implanting more electrodes results in additional electrode pairs, allowing measurement of additional sense vectors.

Switch matrix 84 is used to select which of the available electrodes are coupled to wide band (2.5–100 Hz) amplifier 86 for use in signal analysis. Signal analysis may be performed using analog circuitry, digital circuitry or a combination of both.

Selection of electrodes is controlled by the microprocessor 78 via data/address bus 76. The selection of electrodes may be varied as desired. Signals from the electrodes selected for coupling to band-pass amplifier 86 are provided to multiplexer 88, and thereafter converted to multi-bit digital signals by analog-to-digital (A/D) converter 90, for storage in random access memory 80 under control of direct memory access circuit 82.

The implanted device includes one or more input/output devices 114, by which the device communicates with the patient, a physician, a specialist or an external device. Input/output devices may include a telemetry system that uses radio frequency modulation or ultrasound. The telemetry system may communicate with an external transceiver, which may report data to the patient or physician. The external transceiver may also interface to a communications network, allowing data to be reported remotely. Some implanted devices may include an audible alarm that sounds or a vibrating element that activates when a potentially serious event occurs.

Much of the circuitry in FIG. 2 is dedicated to the provision of cardiac pacing, cardioversion and defibrillation therapies. An exemplary apparatus comprises pacer timing/control circuitry 70, which includes programmable digital counters that control the basic time intervals associated with DDD, VVI, DVI, VDD, AAI, DDI and other modes of single- and dual-chamber pacing. Pacing circuitry 70 also controls escape intervals associated with anti-tachyarrhythmia pacing in both the atrium and the ventricle, employing any of a number of anti-tachyarrhythmia pacing therapies.

Intervals defined by pacing circuitry 70 include: atrial and ventricular pacing escape intervals; the refractory periods during which sensed P-waves and R-waves are ineffective to restart timing of the escape intervals; and the pulse widths of the pacing pulses. The durations of these intervals are determined by microprocessor 78, in response to stored data in memory 80 and are communicated to pacing circuitry 70 via address/data bus 76. Pacing circuitry 70 also determines the amplitude of the cardiac pacing pulses under control of microprocessor 78.

During pacing, the escape interval counters within pacer timing/control circuitry 70 are reset upon sensing of P-waves and R-waves as indicated by a signals on lines 62 and 68, and in accordance with the selected mode of pacing on time-out trigger generation of pacing pulses by pacer output circuitry 72 and 74, which are coupled to electrodes 50, 52, 54 and 56. The escape interval counters are also reset on generation of pacing pulses, and thereby control the basic timing of cardiac pacing functions, including anti-tachyarrhythmia pacing. The durations of the intervals defined by the escape interval timers are determined by microprocessor 78, and are supplied via data/address bus 76. The value of the count present in the escape interval counters when reset by sensed R-waves and P-waves may be used to measure the durations of R—R intervals, P—P intervals, P-R intervals and R-P intervals, which measurements are stored in memory 80 and used to detect the presence of tachyarrhythmias.

Microprocessor 78 typically operates as an interrupt-driven device, under control of a stored program in its read only memory and is responsive to interrupts from pacer timing/control circuitry 70 corresponding to the occurrence sensed P-waves and R-waves and corresponding to the generation of cardiac pacing pulses. These interrupts are provided via data/address bus 76. Any necessary mathematical calculations to be performed by microprocessor 78 and any updating of the values or intervals controlled by pacer timing/control circuitry 70 take place following such interrupts.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 78 into pacer timing/control circuitry 70. In the event that generation of a cardioversion or defibrillation pulse is required, microprocessor 78 employs an escape interval counter to control timing of such cardioversion and defibrillation pulses, as well as associated refractory periods.

In response to the detection of atrial or ventricular fibrillation or tachyarrhythmia requiring a cardioversion pulse, microprocessor 78 activates cardioversion/defibrillation control circuitry 92, which initiates charging of high voltage capacitors 108 and 110 via charging circuit 112, under control of high voltage charging control lines 100. The voltage on high voltage capacitors 108 and 110 is monitored via VCAP line 98, which is passed through multiplexer 88 and in response to reaching a predetermined value set by microprocessor 78, results in generation of a logic signal on Cap Full (CF) line 114, terminating charging. Thereafter, timing of the delivery of the defibrillation or cardioversion pulse is controlled by pacer timing/control circuitry 70. Following delivery of the fibrillation or tachyarrhythmia therapy the microprocessor then returns the device to cardiac pacing and awaits the next successive interrupt due to pacing or the occurrence of a sensed atrial or ventricular depolarization.

Delivery of the cardioversion or defibrillation pulses is accomplished by output circuit 94, under control of control circuitry 92 via control bus 96. Output circuit 94 determines whether a monophasic or biphasic pulse is delivered, the polarity of the electrodes and which electrodes are involved in delivery of the pulse. Output circuit 94 also includes high voltage switches that control whether electrodes are coupled during delivery of the pulse. Alternatively, electrodes intended to be coupled during the pulse may simply be permanently coupled to one another, either exterior to or interior of the device housing, and polarity may similarly be pre-set, as in some implantable defibrillators.

Treatment such as defibrillation, cardioversion or pacing depends upon evaluation of cardiac signals by pacer timing/control circuitry 70. Pacer timing/control circuitry 70 evaluates the signals, at least in part, upon signals on P-out line 62 and R-out line 68. Sense amplifiers 58 and 64 generate signals on P-out line 62 and R-out line 68 in response to A-EGM or V-EGM signals received via electrodes 50, 52, 54 and 56.

Sense amplifiers 58 and 64 generate signals on P-out line 62 and Rout line 68 by amplifying and filtering the EGM signals, and comparing them to sense thresholds. The comparison takes into account whether the magnitude of the signal exceeds or does not exceed the sense threshold. The peak value of the signal is not important to the comparison, nor is the degree by which the signal magnitude exceeds the threshold.

It is important, therefore, that the sense thresholds be set appropriately for the signal magnitudes. If a sense threshold is too high, for example, there is a risk that a valid P-wave or R-wave may be undersensed. One potential consequence of undersensing is that the patient may not receive appropriate therapy.

The invention provides techniques for monitoring the magnitudes of sensed cardiac signals, particularly the attenuation of cardiac signals over long periods of time. Monitoring provides for early detection of signal attenuation that may lead to undersensing.

In general, long-term monitoring of signal attenuation comprises capturing and recording a plurality of peak values, each peak value representing the maximum amplitude of a single representative cardiac cycle. One peak value is recorded per time period. For example, one representative peak value is recorded per day.

Figure 3:
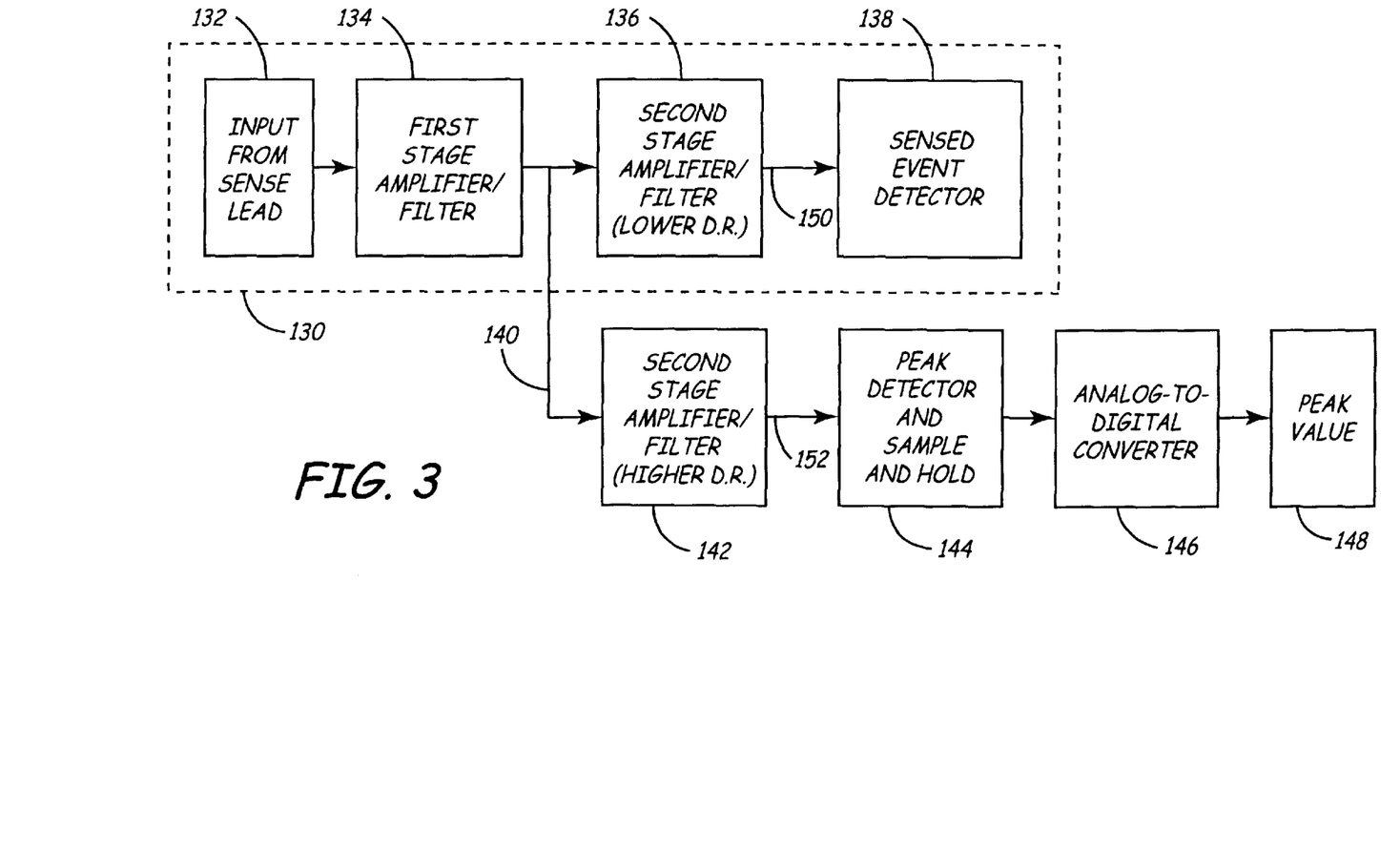
FIG. 3 is a block diagram illustrating techniques for capture of a peak value of a cardiac signal.

FIG. 3 is a block diagram illustrating capturing of a peak value. Sense amplifier 130 receives a cardiac EGM signal 132 from a sense lead. The signal is for a single cardiac cycle. Sense amplifier 130 may receive an A-EGM signal, like sense amplifier 58 in FIG. 2, or a V-EGM signal, like sense amplifier 64. The cardiac signal undergoes first stage amplification and filtering 134. Ordinarily, first stage filter 134 is a band-pass filter. The output of first stage filter 134 is filtered signal 140.

Filtered signal 140 follows two parallel processing paths. In one path, the signal continues through sense amplifier 130, where filtered signal 140 is further amplified and filtered by second stage band-pass filter 136. Signal 150 is then transmitted to sensed event detector 138 and is compared to a sense threshold. Sensed event detector 138 may generate a signal on P-out line 62 or R-out line 68 whenever the magnitude of signal 150 exceeds the atrial sense threshold or ventricular sense threshold, respectively. In this signal path, the peak value of signal 150 and the extent by which the magnitude of signal 150 exceeds the threshold are not important.

The peak value of the signal is captured in an alternate path. To capture the peak value, input signal for a cardiac cycle 132 undergoes first stage filtering and amplification 134. Filtered signal 140 is then received by alternate second stage amplifier and filter 142, which has substantially the same pass band as second stage filter 136. Alternate second stage amplifier and filter 142 has a lower gain and therefore a higher dynamic range than second stage amplifier 136.

The signal is then subjected to peak detector and sample and hold circuit 144, which holds the maximum amplitude. The maximum amplitude is converted to peak value 148 with analog-to-digital converter 146. Peak value 148 is a digital value representing the highest magnitude of the signal for that cardiac cycle.

Notably, peak value 148 represents the maximum of filtered signal 152, rather than the maximum of raw input signal 132. In addition, signals 150 and 152 have substantially the same frequency components, and one signal is the scaled version of the other. Accordingly, peak value 148 is directly proportional to the maximum value of signal 150.

The techniques for capturing peak value may be embodied differently from those shown in FIG. 3. For example, FIG. 3 shows peak detection as an analog technique, followed by conversion of the peak to a digital value. The same results may be obtained by converting cardiac cycle signal 152 to a digital representation, then selecting the largest digital value as the peak.

Figure 4:
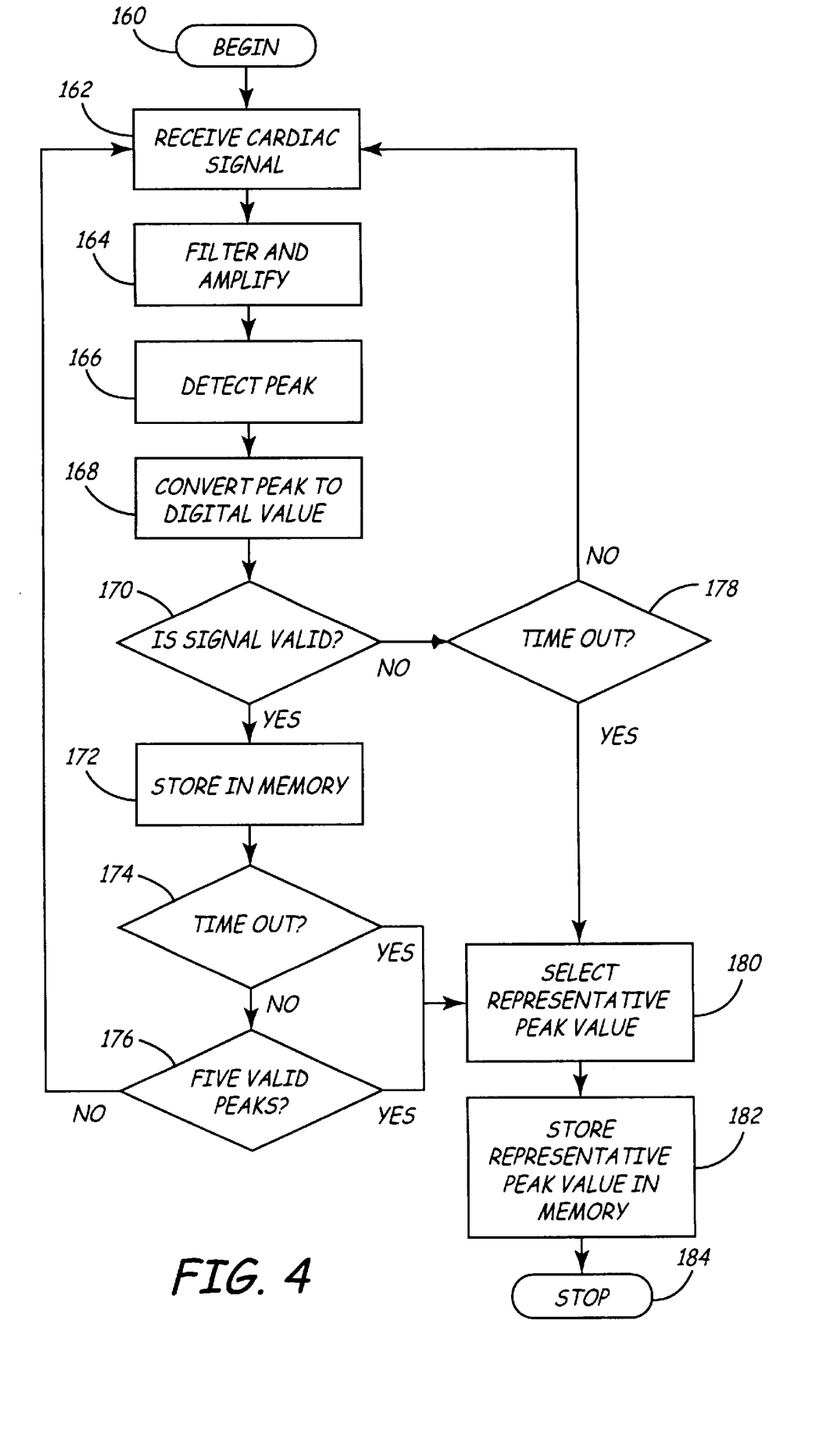
FIG. 4 is a flow diagram illustrating collection of peak values and selection of a representative peak value.

FIG. 4 illustrates how a representative peak value may be selected from a plurality of peak values. For purposes of illustration, it will be assumed that, every day at approximately the same time, five peak values will be captured using techniques described above in connection with FIG. 3. From these five peak values, one peak value will be selected as representative for that day.

The implanted device typically includes a chronometer that triggers the selection of a peak value (160). The chronometer may trigger the selection at, for example, an early morning hour such as 3:00 in the morning. The device receives a cardiac signal for a single cardiac cycle (162). The signal may be an atrial signal, a ventricular signal, or both. The signal may also be one or more sense vector signals.

First stage filter 134 amplifies and filters the signal (164). Peak detector 144 detects the peak of the signal (166) and analog-to-digital converter 146 converts the peak to a digital value (168). The signal may be validated (170). Although depicted in FIG. 4 as occurring after peak detection (166) and digital conversion (168), validation (170) may take place at other times. A signal that fails to satisfy a validation criterion is rejected. A signal that satisfies the validation criteria is accepted.

A representative peak signal should reflect a true intrinsic sensed event. Accordingly, application of validation criteria excludes signals that may be associated with events that are not intrinsic sensed events. For example, a signal may be rejected when the signal follows the administration of a pacing pulse. A signal may be rejected when the signal is not associated with normal sinus rhythm, such as when the signal occurs during a premature ventricular contraction or during an episode of fibrillation or tachycardia. The validation criteria applied to atrial signals need not be exactly like the validation criteria applied to ventricular signals. A valid digital peak value may be stored in memory temporarily (172), while up to five valid peak values are captured (176).

Capture of five valid atrial or ventricular peaks may be completed in a matter of seconds. Under some circumstances, however, repeated rejections of invalid signals may extend the time for capturing valid peaks. Accordingly, a time out condition (174, 178) may be implemented, in which peak capture may be terminated after a fixed amount of time, even if five valid peaks have not been captured.

When capturing peak values terminates, a representative peak value for the valid peak values is selected (180). The representative peak value may be stored in memory (182), and the other peak values may be discarded. The selection of the representative peak value is completed (184), but the process may be performed again in approximately twenty-four hours.

Various modifications may be made to the above techniques. For example, more or fewer than five valid peaks may be accepted. The peaks may be captured at time periods other than once a day, such as twice a day or once every other day. The invention encompasses all of these variations.

Figure 5:
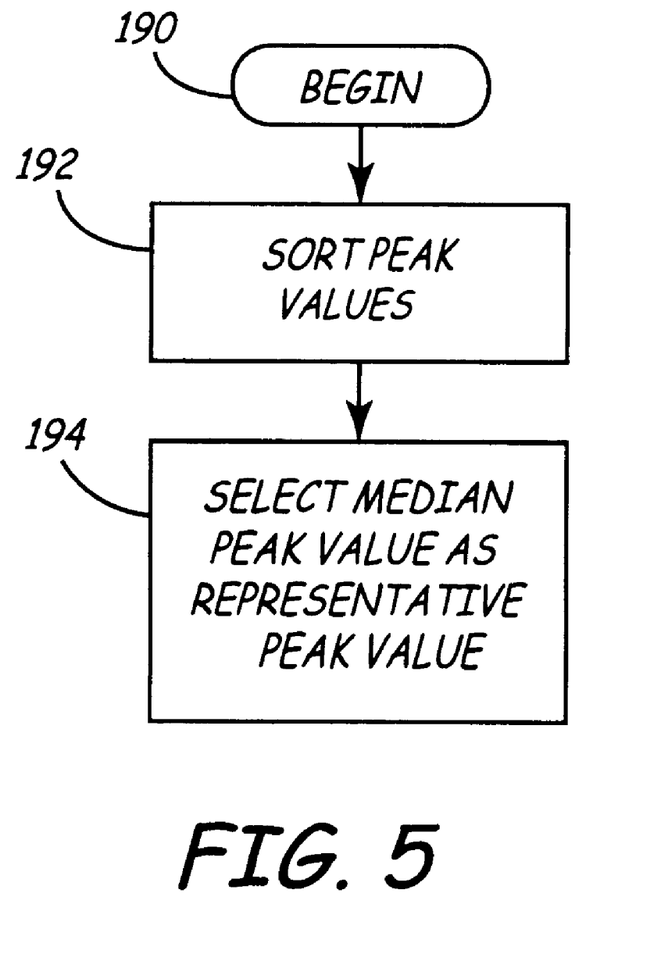
FIG. 5 is a flow diagram illustrating one technique for selection of a representative peak value.

FIG. 5 illustrates a technique for selecting a representative peak value for the time period. Several peak values may have been captured. The peak values are sorted by magnitude (192) and the median value is selected as the representative peak value for the time period (194). For example, if five peak values have been captured, the values are sorted and the third peak value is selected as the representative peak value. The selected representative peak is then stored in memory (182).

The technique may contemplate contingencies when an even number of peak values has been captured. For example, if four peak values have been captured and sorted, the second peak may be selected as the representative peak value. Alternatively, the third peak value may be selected, or a value midway between the second and third peak values may be computed and selected as the representative peak value. The technique may also contemplate contingencies when no peak values have been captured.

The techniques described above may be implemented by analog or digital components, and may use existing systems or specially dedicated subsystems. In the ICD shown in FIG. 2, for example, techniques such as validation (170) or selection of a representative peak value for a plurality of peak values (180) may be performed by microprocessor 78 or by a specially dedicated processor not shown in FIG. 2. Representative peak values may be stored in memory 80 or in another memory element not shown in FIG. 2.

Figure 6:
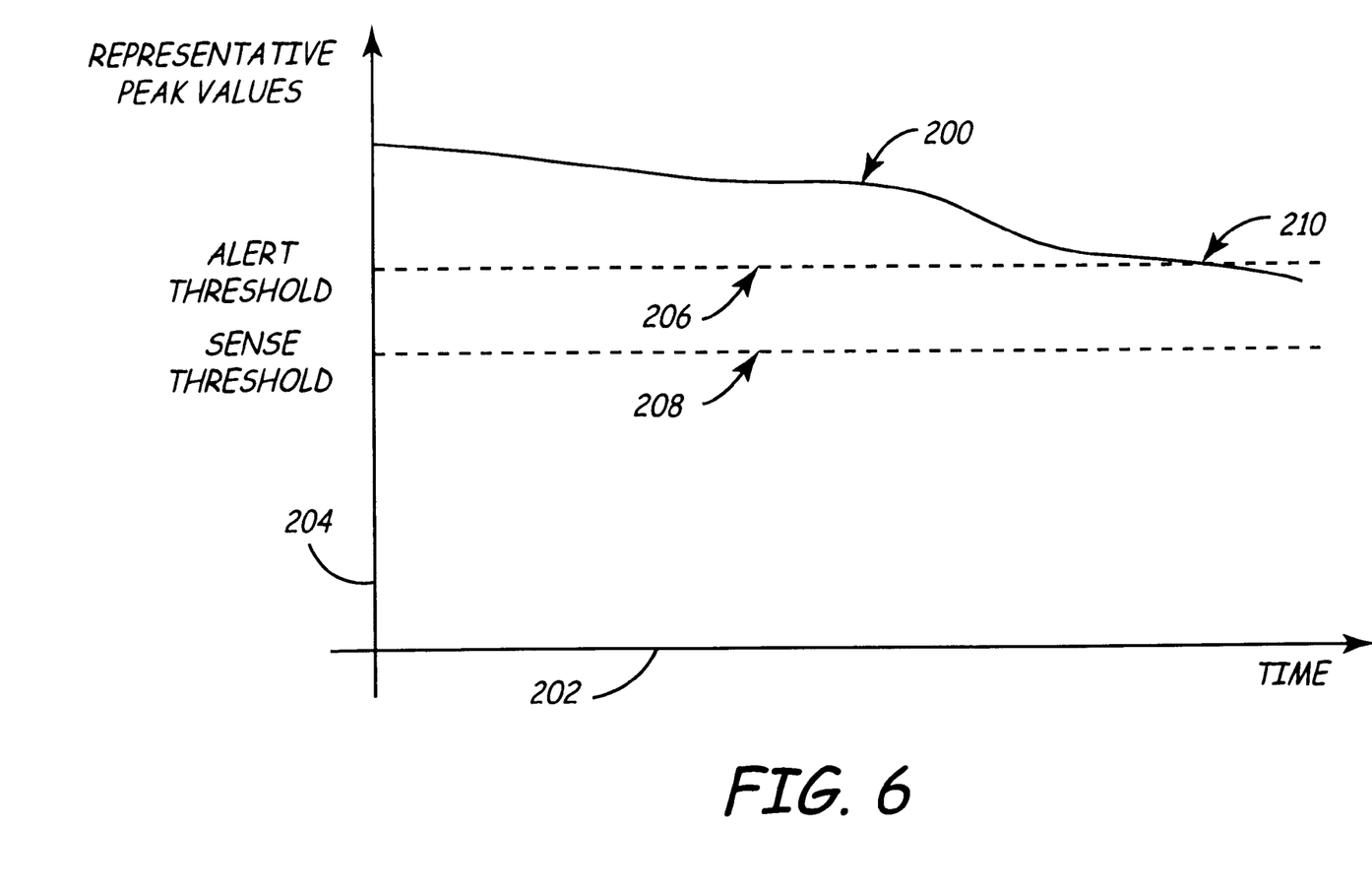
FIG. 6 is a graph of representative peak values as a function of time.

FIG. 6 illustrates one presentation of representative peak values 200 collected over time. The peak values may be atrial peak values or ventricular peak values. Magnitudes 204 of the peak values are plotted over time 202. Typical units of time for time scale 202 are months.

Peak values curve 200 manifests an attenuation in signal magnitude over a long period. The attenuation brings peak values closer to a magnitude 208 at which a typical peak value will not exceed a sense threshold, and as a result will not be detected as a cardiac event. Consequently, as typical signal magnitudes decline over time, there is an increased risk that the medical device will be unable to sense a valid cardiac signal, due to the failure of the signal to exceed the sense threshold.

Before peak values curve 200 approaches sense threshold level 208, peak value curve may cross 210 alert threshold 206, which has a magnitude above sense threshold 208. When peak values curve 200 crosses 210 alert threshold 206, the implanted device may issue an alert.

An alert may be implemented in many ways. An implementation of the invention may include a plurality of alert thresholds, with the form of alert depending upon which alert threshold was crossed. For example, a modest attenuation may result in an alert to the patient's physician during a routine check-up. A more severe attenuation may result in the sounding of an audible alarm that can be heard by the patient, and which advises the patient to seek medical attention promptly. The patient may simply visit his physician, who obtains a report of representative peak values from the device. The device may also support remote communication, in which the device reports to the physician by telephone or other communication system, without the need for an office visit.

Figure 7:
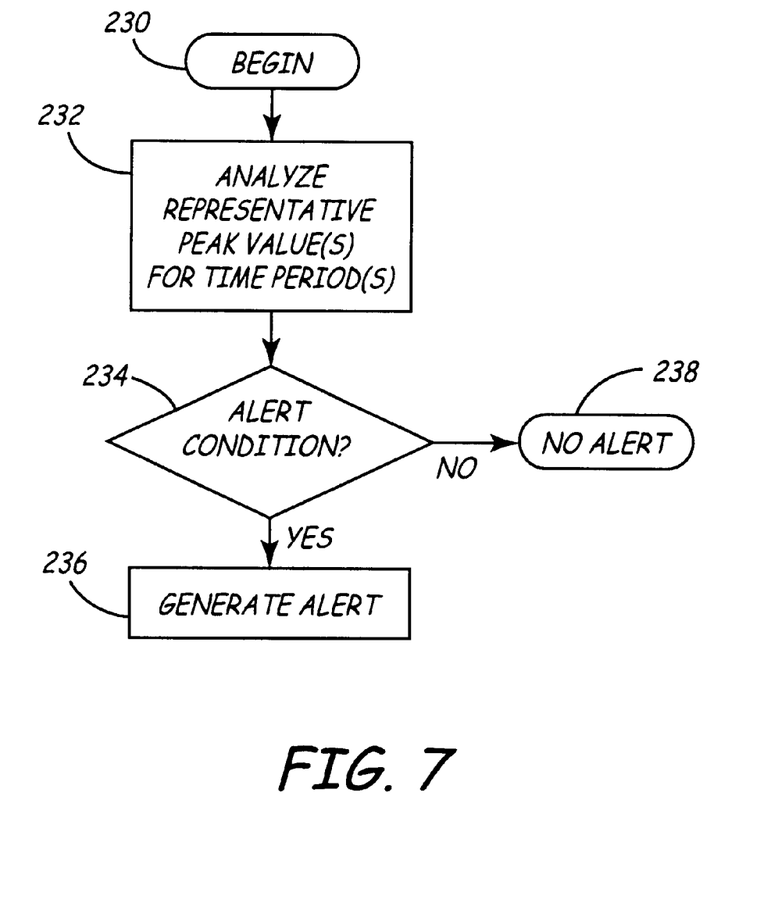
FIG. 7 is a flow diagram illustrating techniques for alerting the patient and/or physician based upon an analysis of representative peak values.

FIG. 7 illustrates techniques for alerting the patient and/or physician based upon an analysis of representative peak values. Analysis may commence (230) at any time, and may be performed automatically or in response to an interrogation. Representative peak values are analyzed for one or more time periods (232). If the analysis indicates signal attenuation, an alert condition may be indicated (236).

As noted above, the magnitude of a peak value falling below alert threshold 206 may give rise to generation of an alert (238). Other conditions, such as the rate of change of peak values over time, also may also give rise to an alert (238). The kind of alert generated may depend upon the alert conditions. If no alert conditions exist, no alert is generated (240).

Figure 8:
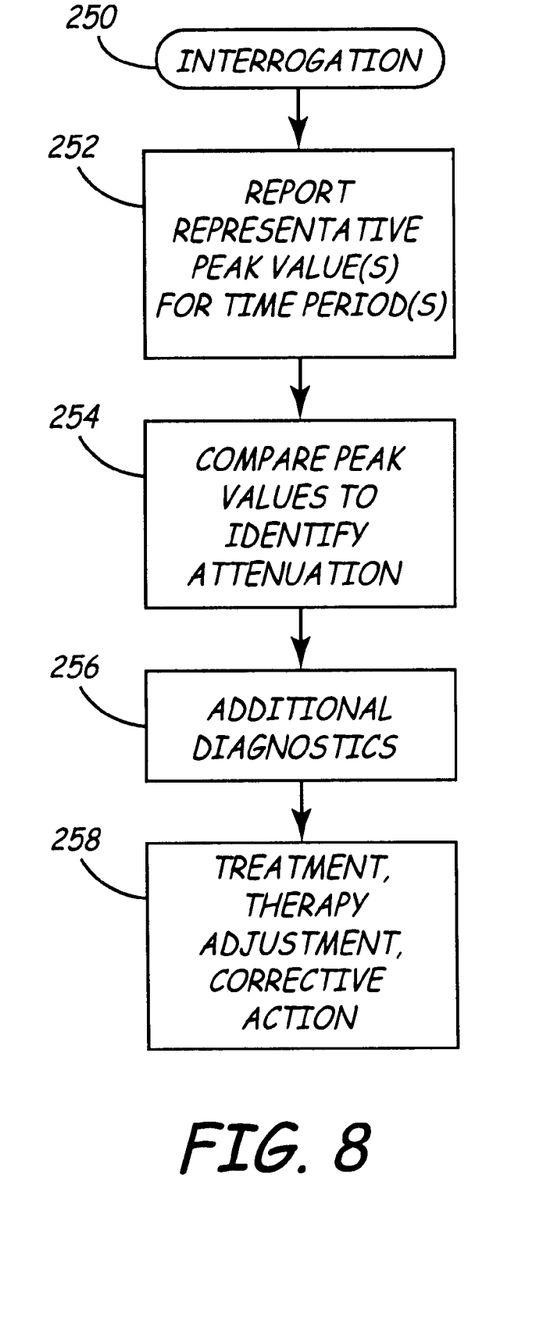
FIG. 8 is a flow diagram showing techniques for reporting to a physician.

FIG. 8 illustrates an example of techniques for reporting representative peak values for signal attenuation to a person such as a physician. Reporting is usually initiated in response to an interrogation (250). Representative peak values are reported for one or more time periods (252). The report compares representative peak values to each other to identify signal attenuation (254). Examples of comparative reports include a graphical report similar to FIG. 6, or a report in a tabular format.

In many instances, the report will not tell the physician the exact cause of the signal attenuation. For example, the report may not definitively demonstrate that signal attenuation is caused by a shift in electrode position, rather than a change in the cardiac substrate. Consequently, the physician may be prompted to perform additional diagnostic procedures (256) to evaluate the problem. Based upon the report and the results of the other diagnostics, appropriate action may be taken (258).

The action that is appropriate generally depends upon the reason for the signal attenuation. If the patient's cardiac tissue has been damaged, for example, appropriate action may include treatment for the condition. If the position of the electrode has shifted, appropriate action may include therapy adjustment, such as an adjustment to the sense thresholds. In some circumstances, the implanted device may automatically adjust sense thresholds to enhance the sensitivity of the device to EGM signals. In patients having multiple electrode pairs, appropriate action may include changing sense vectors. If the electrode has failed, appropriate action may include replacing the electrode. The invention, therefore, may assist the patient and the physician in diagnosing physiologic conditions, establishing therapy, and troubleshooting the implanted device.

The invention offers advantages and uses as well. The peak values may be used, for example, to adjust sense thresholds automatically, to trigger automatic troubleshooting diagnostics within the device, or to change sense vectors automatically. The peak values may be used by the physician to monitor the progression of disease, or to correlate representative peak values with other cardiac conditions, such as arrhythmia. In addition, the invention offers the advantage of making the measurements of the peak values automatically, usually without any disturbance to the patient.

Although the invention is useful for monitoring changes to peak values that occur slowly over long periods of time, the invention is not limited to monitoring long-term changes. The invention is also useful for monitoring short-term changes in signal amplitude. A change in amplitude within a short time may occur, for example, when there is an abrupt change in the position of a sensing electrode.

Various embodiments of the invention have been described. Various modifications may be made without departing from the scope of the claims. For example, a representative peak value for a time period may be selected by mathematical techniques, such as by computing the arithmetic mean or the arithmetic mean of the captured peak values.

The invention may also be extended to monitor additional chambers of the heart. A patient may have an ICD that extends sensing electrodes in the right atrium, the right ventricle and the left ventricle, for example. The ICD in this patient would receive an A-EGM, a right V-EGM (RV-EGM) and a left V-EGM (LV-EGM). The techniques the invention may be applied independently to the R-wave peaks in the RV-EGM and the LV-EGM. These embodiments are illustrative of the practice of the invention. These and other embodiments are within the scope of the following claims.

What is claimed is:

1. A method comprising:
    filtering a first signal of a first single cardiac cycle sensed by an electrode;
    generating a first digital peak value as a function of the magnitude of the peak of the first filtered signal;
    filtering a second signal of a second single cardiac cycle sensed by the electrode;
    generating a second digital peak value as a function of the magnitude of the peak of the second filtered signal; and
    selecting a representative digital value as a function of the first peak digital value and the second peak digital value.

2. The method of claim 1, further comprising storing the first digital peak value in memory.

3. The method of claim 1, further comprising detecting the peak of the first filtered signal.

4. The method of claim 1, further comprising:
    validating the first signal according to a validation criterion; and
    rejecting the first signal when the first signal fails to satisfy the validation criterion.

5. The method of claim 1 further comprising:
    comparing the representative digital value to an alert threshold; and
    generating an alert when the representative digital value falls below the alert threshold, the alert notifying at least one of a patient and a physician.

6. The method of claim 1, wherein the first digital peak value corresponds to one of a P-wave and an R-wave.

7. The method of claim 1, further comprising:
    filtering a third signal of a third single cardiac cycle sensed by the electrode;
    generating a third digital peak value as a function of the magnitude of the peak of the third filtered signal;
    filtering a fourth signal of a fourth single cardiac cycle sensed by the electrode;
    generating a fourth digital peak value as a function of the magnitude of the peak of the fourth filtered signal;
    filtering a fifth signal of a fifth single cardiac cycle sensed by the electrode;
    generating a fifth digital peak value as a function of the magnitude of the peak of the fifth filtered signal; and
    selecting the median digital peak value from the digital peak values.

8. A method comprising:
    filtering a first signal of a first single cardiac cycle sensed by an electrode in a first time period;
    generating a first digital peak value as a function of the magnitude of the peak of the first filtered signal;

filtering a second signal of a second single cardiac cycle sensed by the electrode in a second time period;

generating a second digital peak value as a function of the magnitude of the peak of the second filtered signal; and reporting an output as a function of the first digital value and the second digital value; and comparing the peak values to identify a change in the cardiac signals.

9. The method of claim 8, wherein reporting an output comprises reporting the first digital value and the second digital value.

10. The method of claim 8, further comprising:
selecting the first digital peak value from a first plurality of digital peak values generated in the first time period; and
selecting the second digital peak value from a second plurality of digital peak values generated in the second time period.

11. The method of claim 8, wherein the first time period is approximately twenty-four hours after the second time period.

12. The method of claim 8, further comprising generating an alert.

13. The method of claim 8, further comprising adjusting a sense threshold.

14. The method of claim 8, wherein comparing the peak values to identify a change in the cardiac signals comprises comparing the peak values to identify attenuation in the cardiac signals.

15. A device comprising:
a first filter that receives a single cardiac cycle signal sensed by an electrode implanted in a heart and generates a first filtered cardiac signal;
a second filter that receives the first filtered cardiac signal and generates a second filtered cardiac signal;
a peak detector that senses the peak of the second filtered cardiac signal;
a sample-and-hold circuit that captures the magnitude of the peak of the second filtered cardiac signal; and
an analog-to-digital converter that generates a digital peak value as a function of the magnitude of the peak.

16. The device of claim 15, further comprising a third filter that receives the first filtered cardiac signal and generates a third filtered cardiac signal, wherein the second filter and the third filter comprise band-pass filters, the second filter having a higher dynamic range than the third filter.

17. The device of claim 15, further comprising memory that stores the digital peak value.

18. The device of claim 15, further comprising a processor that accepts the peak value when the cardiac cycle signal satisfies a validation, criterion and rejects the cardiac cycle signal when the signal fails to satisfy the validation criterion.

19. The device of claim 15, further comprising a processor that selects a representative peak value from a plurality of peak values.

20. A method comprising:
selecting, within a first time period, a first peak value of a filtered electrogram signal for a cardiac cycle from a first plurality of peak values; and
selecting, within a second time period, a second peak value of a filtered electrogram signal for a cardiac cycle from a second plurality of peak values, wherein the first peak value is representative of the first plurality of peak values, and the second peak value is representative of the second plurality of peak values, and wherein the first peak value is the median of the first plurality of peak values.

21. A method comprising:
selecting, within a first time period, a first peak value of a filtered electrogram signal for a cardiac cycle from a first plurality peak values; and
selecting, within a second time period, a second peak value of a filtered electrogram signal for a cardiac cycle from a second plurality of peak values, wherein the first plurality of peak values comprises five peak values.

22. A method comprising:
selecting, within a first time period, a first peak value of a filtered electrogram signal for a cardiac cycle from a first plurality of peak values;
selecting, within a second time period, a second peak value of a filtered electrogram signal for a cardiac cycle from a second plurality of peak values: and reporting the first peak value and the second peak value.

23. A method comprising:
selecting, within a first time period, a first peak value of a filtered electrogram signal for a cardiac cycle from a first plurality of peak values; and
selecting, within a second time period, a second peak value of a filtered electrogram signal for a cardiac cycle from a second plurality of peak values, wherein each of the first plurality of peak values comprises the maximum amplitude of a filtered electrogram signal for a cardiac cycle within the first time period, and each of the second plurality of peak values comprises the maximum amplitude of a filtered eleotrogram signal for a cardiac cycle within the second time period, and wherein each of the first and second pluralities of peak values corresponds to one of a P-wave and an R-wave.

24. A method comprising:
selecting, within a first time period, a first peak value of a filtered electrogram signal for a cardiac cycle from a first plurality of peak values; and
selecting, within a second time period, a second peak value of a filtered electrogram signal for a cardiac cycle from a second plurality of peak values, wherein each of the first plurality of ask values corn rises the maximum amplitude of a filtered electrogram signal for a cardiac cycle within the first time period, and each of the second plurality of peak values comprises the maximum amplitude of a filtered electrogram signal for a cardiac cycle within the second time period, and wherein the first time period is approximately twenty-four hours after the second time period.

25. A method comprising:
selecting, within a first time period, a first peak value of a filtered electrogram signal for a cardiac cycle from a first plurality of peak values; and
selecting, within a second time period a second peak value of a filtered electrogram signal for a cardiac cycle from a second plurality of peak values; and
comparing the first peak value to the second peak value to identify a change in the filtered electrogram signals.

26. A method comprising:
sensing a first plurality of cardiac signals;
selecting a first representative digital value for the first plurality of cardiac signals;
sensing a second plurality of cardiac signals;
selecting a second representative digital value for the second plurality of cardiac signals; and
comparing the representative digital values to identify a change in the cardiac signals.

27. The method of claim 26, wherein selecting a first representative digital value for the first plurality of cardiac signals comprises:

generating a plurality of digital peak values as a function of magnitudes of the first plurality of cardiac signals; and selecting the first representative digital value from among the plurality of digital peak values.

28. The method of claim 26, further comprising:

sensing the first plurality of cardiac signals in a first time period; and sensing the second plurality of cardiac signals in a second time period.

29. The method of claim 26, wherein the first and second representative digital values corresponds to one of a P-wave and an R-wave.

30. A method comprising:

monitoring digital peak values of a plurality of representative filtered cardiac electrogram signals; and determining whether the magnitudes of the signals are changing over time.

31. The method of claim 30, further comprising adjusting a sense threshold in response to the determination.

32. The method of claim 31, wherein adjusting a sense threshold in response to the determination comprises adjusting the sense threshold downward when the magnitudes of the signals are changing downward.

33. The method of claim 30, wherein a digital peak value of a representative filtered cardiac electrogram signal comprises a median of a second plurality of digital peak values of representative filtered cardiac electrogram signals occurring within a time period lasting less than twenty-four hours.

34. The method of claim 30, further comprising performing a diagnostic to evaluate the cause of a change in signal magnitudes.

* * * * *

UNITED STATES PATENT AND TRADEMARK OFFICE
CERTIFICATE OF CORRECTION

PATENT NO. : 6,721,592 B2
DATED : April 13, 2004
INVENTOR(S) : David Peichel et al.

It is certified that error appears in the above-identified patent and that said Letters Patent is hereby corrected as shown below:

Column 12,
Line 38, after "claim 1" please insert -- , --.

Column 14,
Lines 16 and 17, delete "values; and reporting" and insert -- values; and reporting --.
Line 39, delete "ask values corn rises" and insert -- peak values comprises --.
Line 50, delete "and".

Signed and Sealed this

Ninth Day of November, 2004

JON W. DUDAS
*Director of the United States Patent and Trademark Office*